(12) United States Patent
Leveille

(10) Patent No.: US 10,514,117 B2
(45) Date of Patent: Dec. 24, 2019

(54) FLUIDIC FITTING WITH INTEGRAL FACE SEAL

(71) Applicant: Waters Technologies Corporation, Milford, MA (US)

(72) Inventor: Wade P. Leveille, Douglas, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 274 days.

(21) Appl. No.: 15/709,618

(22) Filed: Sep. 20, 2017

(65) Prior Publication Data
US 2018/0094753 A1 Apr. 5, 2018

Related U.S. Application Data

(60) Provisional application No. 62/404,567, filed on Oct. 5, 2016.

(51) Int. Cl.
*F16L 19/02* (2006.01)
*G01N 30/60* (2006.01)
(Continued)

(52) U.S. Cl.
CPC ........ *F16L 19/0212* (2013.01); *F16L 19/0206* (2013.01); *G01N 30/6026* (2013.01); *F16L 49/02* (2013.01); *G01N 30/22* (2013.01)

(58) Field of Classification Search
CPC ... F16L 19/0206; F16L 19/0212; F16L 19/05; F16L 33/207; F16L 33/2076; G01N 30/6026; G01N 30/6039
See application file for complete search history.

(56) References Cited

U.S. PATENT DOCUMENTS 2,967,068 A * 1/1961 Gressel .............. F16L 19/0206
   285/328
3,197,241 A * 7/1965 Authon .................... F16L 5/00
   285/402
(Continued)

FOREIGN PATENT DOCUMENTS

DE   102009022368 B3   11/2010
EP      3163298 A2 *   5/2017  .......... F16L 19/0206
(Continued)

OTHER PUBLICATIONS

International Search Report and Written Opinion in International Patent Application No. PCT/US17/52382, dated Dec. 4, 2017; 15 pages.
(Continued)

*Primary Examiner* — David Bochna
(74) *Attorney, Agent, or Firm* — Schmeiser, Olsen & Watts LLP; William G. Guerin

(57) ABSTRACT

A fitting for a fluidic coupling includes a tube assembly that includes an inner tube, an intermediate tube formed of a polymeric material and disposed over at least a portion of a length of the inner tube, and an outer tube formed of a metal and disposed over the intermediate tube. The inner tube has an inner tube endface and a first fluid channel. The intermediate tube includes an extruded portion having a length and an intermediate tube endface. The outer tube has an outer tube endface and an outer surface. First and second radial crimps are formed on the outer surface at first and second distances from the outer tube endface and extend for first and second axial lengths, respectively. The inner and outer tube endfaces are co-planar and the intermediate tube endface is separated from the inner and outer tube endfaces by the length of the extruded portion.

17 Claims, 10 Drawing Sheets

(51) Int. Cl.
*F16L 49/02* (2006.01)
*G01N 30/22* (2006.01)

(56) References Cited

U.S. PATENT DOCUMENTS

| | | |
|---|---|---|
| 5,782,500 A | 7/1998 | Mate |
| 5,934,711 A * | 8/1999 | Gady ..................... F16L 47/24 |
| | | 285/351 |
| 2013/0126021 A1 * | 5/2013 | Hobbs ................ G01N 30/6039 |
| | | 137/557 |
| 2015/0369403 A1 | 12/2015 | Cormier et al. |
| 2017/0254452 A1 * | 9/2017 | Stearns ............... F16L 19/0206 |

FOREIGN PATENT DOCUMENTS

| | | | | |
|---|---|---|---|---|
| FR | 2775053 A1 * | 8/1999 | .......... | F16L 19/0206 |
| WO | 0173338 A1 | 10/2001 | | |
| WO | 2012116753 A1 | 9/2012 | | |
| WO | WO-2013032832 A1 * | 3/2013 | ......... | G01N 30/6052 |
| WO | 2013072755 A1 | 5/2013 | | |

OTHER PUBLICATIONS

International Preliminary Report on Patentability in PCT/US2017/052382 dated Apr. 18, 2019; 8 pages.

* cited by examiner

FLUIDIC FITTING WITH INTEGRAL FACE SEAL

RELATED APPLICATIONS

This application claims priority to U.S. Provisional Application No. 62/404,567 filed on Oct. 5, 2016, and titled "FLUIDIC FITTING WITH INTEGRAL FACE SEAL," the entirety of which is incorporated by reference herein.

FIELD OF THE INVENTION

The invention relates generally to fluidic couplings such as those used in chromatographic systems. More particularly, the invention relates to a fluidic fitting having an integral face seal.

BACKGROUND

Chemical analysis systems often include fluid channels that accommodate high pressures. For example, a liquid chromatography system, such as a system designed for ultra performance liquid chromatography (UPLC®), can operate at pressure that may exceed 18,000 psi. The fluid channels in such systems may include tubing that is coupled to other components or tubing using a conventional coupling such as a standard compression fitting.

The improved performance of UPLC systems includes substantial increases in separation power. Adverse chromatographic effects such as carryover and peak tailing can result from the use of conventional couplings used to achieve fluid-tight seals and are more readily observable in system measurements. In typical couplings, the seal is formed along the side of the capillary. For example, many couplings use an annular sealing element such as a ferrule that has a conical outer surface. To form a fluid-tight coupling, a capillary having the annular sealing element displaced away from the endface is inserted into a receptacle of a coupling body. The receptacle is defined by a cylindrical bore that transitions to a conical bore and then to a smaller diameter cylindrical bore. A fluid channel extends from the surface at the bottom of the smaller diameter cylindrical bore into the coupling body. The cone angle of the conical bore is greater than the cone angle of the annular sealing element resulting in a seal along the circumferential contact between the annular sealing element and the conical surface of the conical bore. Additional force applied by a compression screw after achieving initial contact between the annular sealing element and conical bore surface results in a contact seal between the annular sealing element and the outer surface of the capillary. If the endface of the capillary is not in contact with the bottom of the cylindrical bore, the region between the outer surface of the capillary and the side wall of the smaller cylindrical bore below the circumferential contact seal represents an unswept volume. During a chromatographic measurement, analytes can become trapped in the unswept volume and gradually diffuse into the fluid flow, thereby degrading the chromatographic measurement data. Moreover, corrosion may occur at the capillary interface, leading to further degradation of chromatographic measurements.

SUMMARY

In one aspect, the invention features a fitting for a fluidic coupling. The fitting includes an inner tube, an intermediate tube and an outer tube. The inner tube has an inner tube endface and a first fluid channel. The intermediate tube is formed of a polymeric material and is disposed over at least a portion of a length of the inner tube. The intermediate tube includes an extruded portion having a length and an intermediate tube endface. The outer tube is formed of a metal and is disposed over the intermediate tube. The outer tube has an outer tube endface and an outer surface, a first radial crimp on the outer surface at a first distance from the outer tube endface that extends for a first axial length, and a second radial crimp on the outer surface at a second distance from the outer tube endface that extends for a second axial length. The outer tube endface is co-planar with the inner tube endface. The intermediate tube endface is separated from the inner tube endface and the outer tube endface by the length of the extruded portion.

In another aspect, the invention features a method of forming a fitting for a fluidic coupling. The method operates on a tube assembly that includes an inner tube having an inner tube endface and a fluid channel, an intermediate tube formed of a polymeric material and disposed over at least a portion of a length of the inner tube and having an intermediate tube endface, and an outer tube formed of a metal and disposed over the intermediate tube. The outer tube has an outer tube endface and an outer surface. The inner tube endface, intermediate tube endface and outer tube endface re coplanar. The method includes forming a first radial crimp on the tube assembly over a first crimp length at a first distance from the outer tube endface to secure the inner tube, intermediate tube and outer tube to each other and to extrude a portion of the intermediate tube such that the intermediate tube endface is separated from the inner tube endface and the outer tube endface by an extrusion length. The method further includes forming a second radial crimp on the tube assembly over a second crimp length at a second distance from the outer tube endface.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure.

As used herein, a coupling body means a body that has a bore to receive a tube assembly and a fluid channel to receive a fluid from or provide a fluid to the tube assembly. For example, a coupling body can be a structure provided between the endfaces of two capillaries (or tube assemblies) to enable fluid to pass from one capillary to the other capillary. Alternatively, a system component can include a coupling body. By way of examples, an injector valve or a chromatography column for a liquid chromatography system may include a coupling body to couple fluid to or from a capillary or another component of the liquid chromatography system.

A tube assembly refers to at least one tube (e.g., capillary) and additional structure such as a sleeve or a second tube disposed either inside or outside the first tube. A retaining ring, as used herein, includes a ring or clip typically formed of metal and shaped similar to the letter "C," although other shapes, including nominally square, rectangular and tapered cross sectional shapes, may be used. The shape allows the ring to be installed in a crimp or groove on a cylindrical part to limit or prevent axial movement of an axial loading device along the cylindrical part. The retainer ring can open slightly from its original diameter to enable the ring to slide over the full diameter of a tube until the ring moves into the crimp or groove where the ring returns (i.e., "relaxes") to its original shape and diameter. The retaining ring is sometimes referred to as a circlip or a C-clip.

Figure 1:
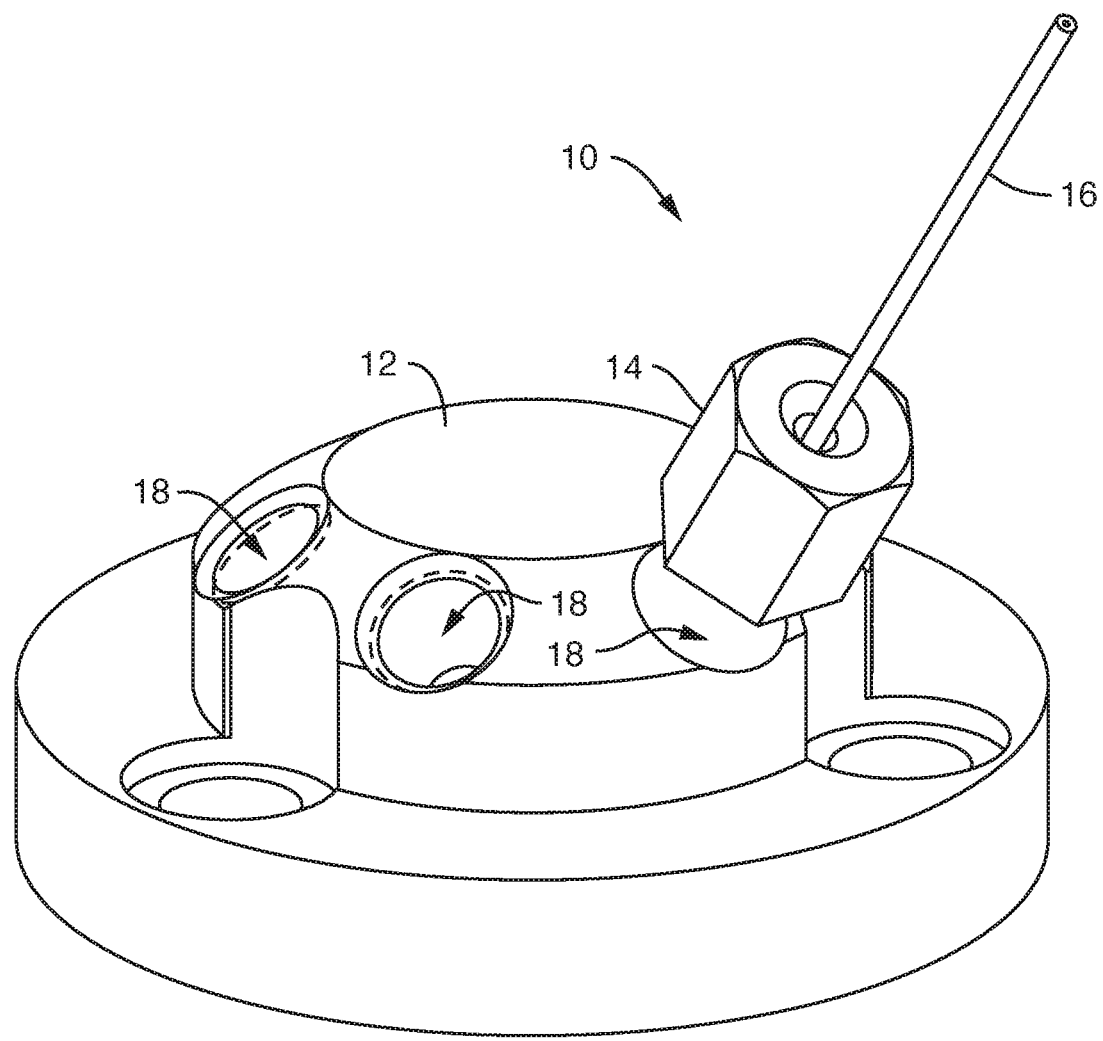
FIG. 1 is an illustration of a capillary coupling at a stator portion of a rotary shear seal valve for a liquid chromatography system.

FIG. 1 shows a view of a capillary coupling 10 at a stator portion 12 of a rotary shear seal valve for a liquid chromatography system. The fluidic coupling 10 includes a compression nut 14 and additional components (not visible). A tube 16 defines a fluid channel that conducts a fluid from a chromatographic system component to one of the stator ports 18 or from the stator port 18 to the chromatographic system component. By way of examples, the chromatographic system component can be an injection valve or a chromatography column. A second fluid channel is defined inside the stator portion 12 and interfaces with a rotor portion of the rotary shear seal valve to couple or decouple the second fluid channel with a third fluid channel in communication with one of the other stator ports 18.

Figure 2A:
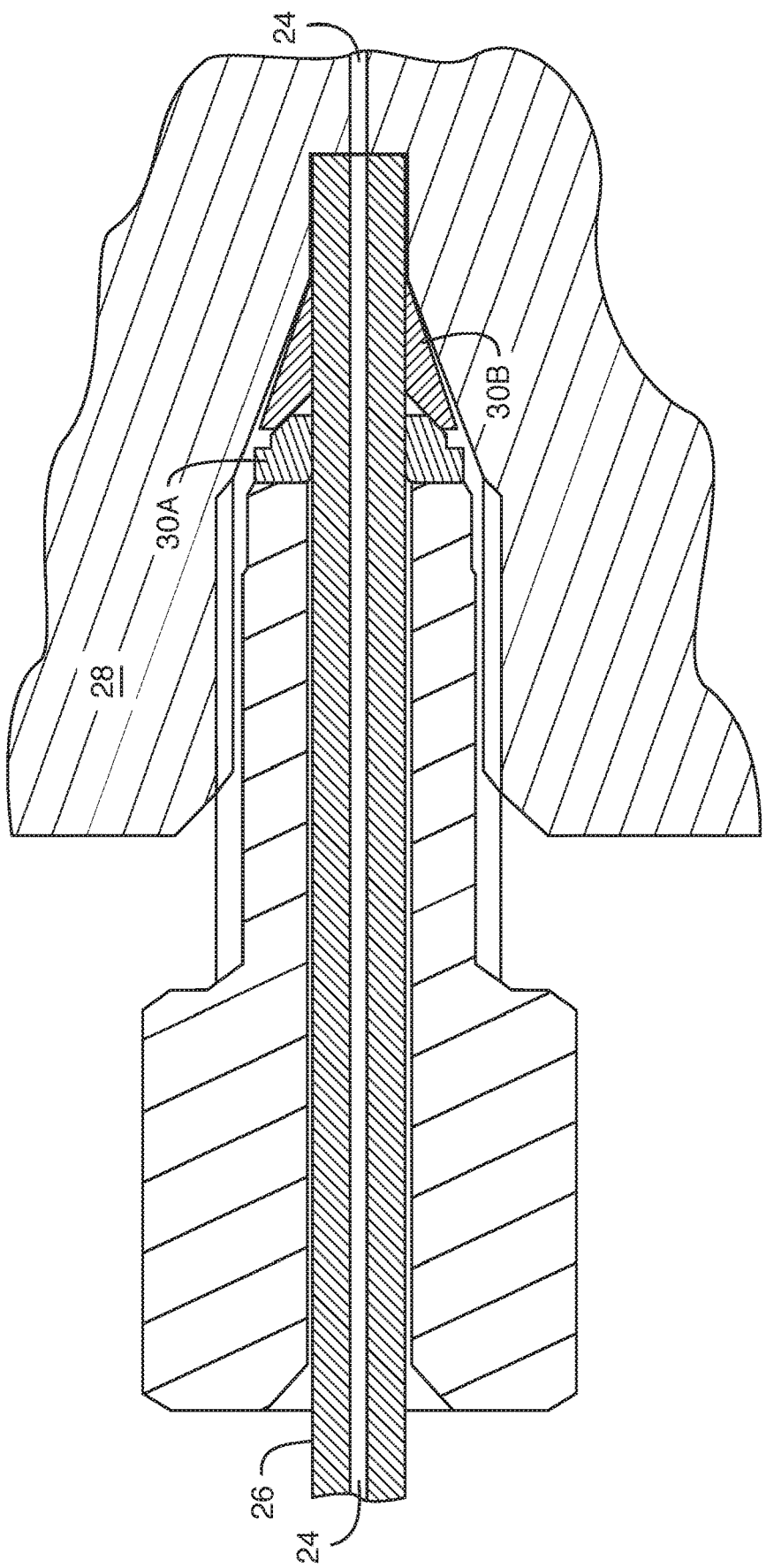
FIG. 2A is a cross-sectional view of a conventional fitting used to couple two fluid channels to each other.
Figure 2B:
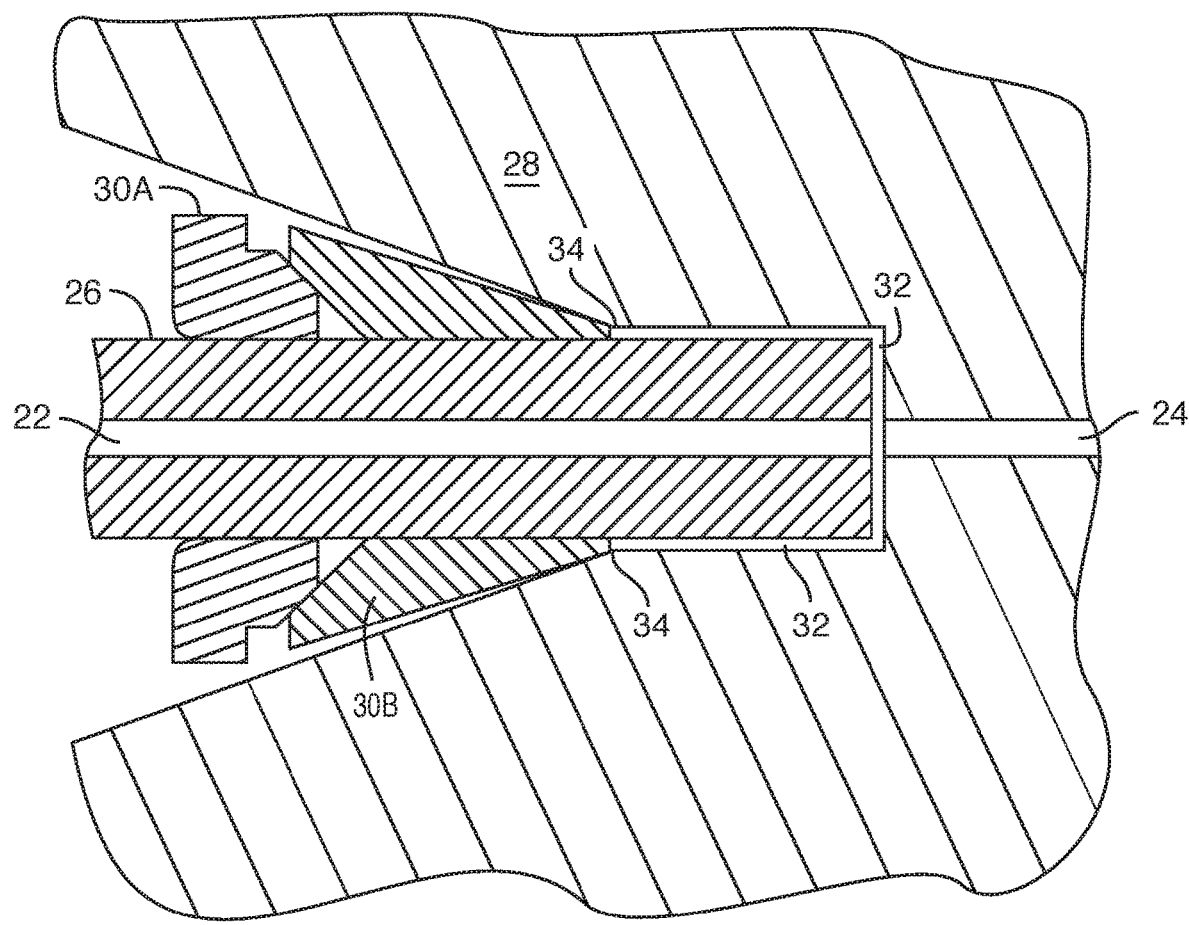
FIG. 2B is an expanded cross-sectional view of a portion of the conventional fitting of FIG. 2A showing the sealing interface.

FIG. 2A shows a cross-sectional view of a conventional fitting 20 that can be used, for example, to couple two fluid channels 22 and 24. For example, the fitting 20 can be used to couple the tube 16 of FIG. 1 to an internal fluid channel in the rotary shear seal valve. The tube 26 includes the first fluid channel 22 which is coupled to the second fluid channel 24 inside the coupling body 28. FIG. 2B is an expanded view of a portion of FIG. 2A that shows the sealing interface. As illustrated, a two-part ferrule 30A and 30B engages an inner conical surface of the coupling body 28 and the outer surface of the tube 26. In other variations, a single part ferrule may be used. The resulting fluidic seal can withstand a high fluid pressure (e.g., greater than 15,000 psi); however, an unswept volume 32 is formed in the unoccupied region of the bore that surrounds the tube 26 and is to the right of the contact zone 34 where the ferrule part 30B is in contact with the conical surface in the figure. The presence of the unswept volume 32 may result in sample carryover. For example, as the sample moves from the first fluid channel 22 into the second fluid channel 24, some of the sample can diffuse into the unswept volume 32. Subsequently, the sample present in the unswept volume 32 can diffuse back into the main fluid flow and into the second fluid channel 24. If the fitting 20 is used with components of a liquid chromatography system, such as illustrated in FIG. 1, the fluid sample that diffuses back into the fluid flow (i.e., the carryover) can adversely affect chromatographic measurements.

Figure 3A:
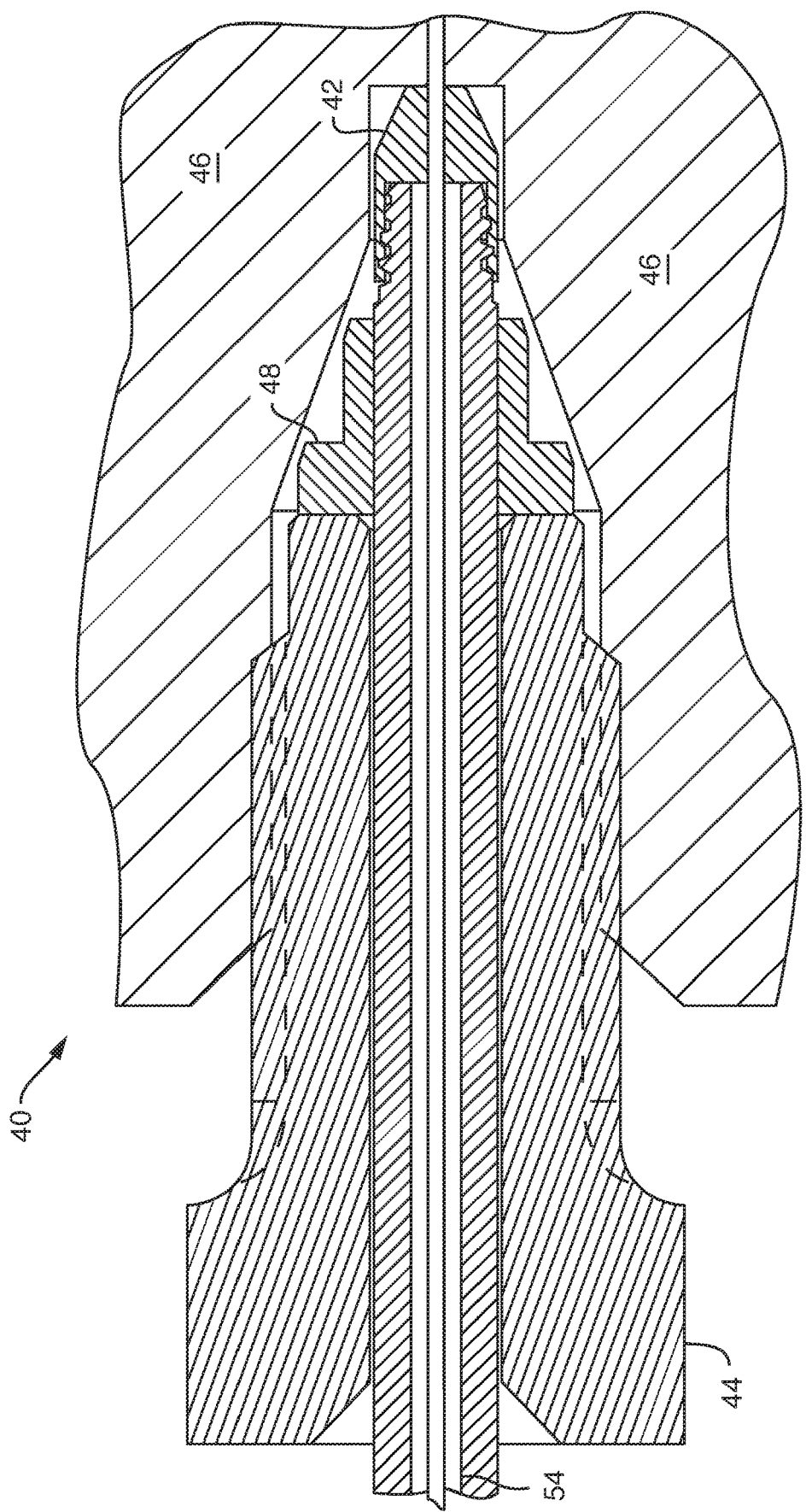
FIG. 3A is a cross-sectional view of a known fluidic coupling.
Figure 3B:
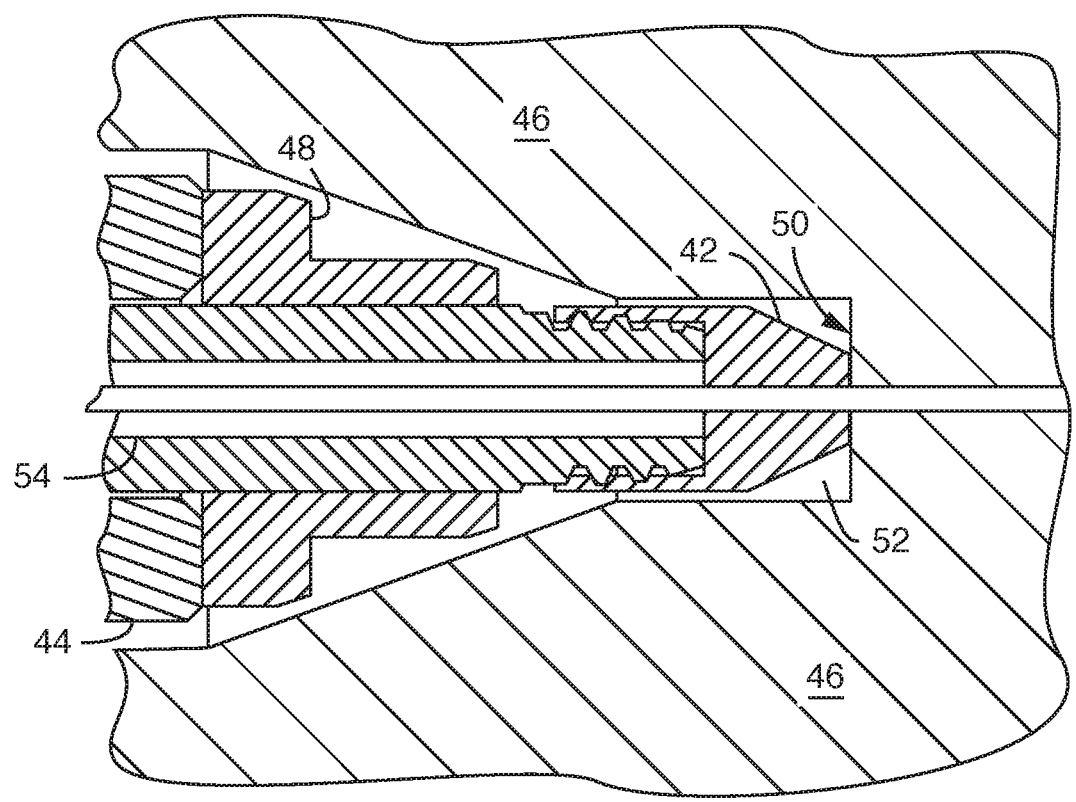
FIG. 3B is an expanded cross-sectional view of the fluidic coupling of FIG. 3A showing an uncompressed coupling seal.

FIG. 3A is a cross-sectional view of a fluidic coupling 40 such as disclosed in U.S. Patent Publication No. 2015/0369403, the disclosure of which is incorporated herein by reference. FIG. 3B is an expanded cross-sectional view of the fluidic coupling 40 in the region of a coupling seal 42. The fluidic coupling 40 includes the coupling seal 42, a tube assembly, a compression screw 44 and a coupling body 46. As the compression screw 44 is rotated so that it advances into the coupling body 46, a surface on the compression screw 44 engages a back surface of a ferrule 48 this is secured to the tube assembly. Continued rotation of the compression screw 44 results in moving the combined ferrule 48 and tube assembly as one further into the receptacle until the coupling seal 42 comes into contact with an internal sealing surface 50 of the coupling body 46. Further rotation results in axial compression of the coupling seal 42 such that coupling seal 42 deforms and flows into an unoccupied volume 52 of the coupling body 46. This deformation and flow into the unoccupied volume 52 prevents compression of the capillary 54 or damage to the capillary 54.

While providing a fluid tight seal for many applications, the fluidic coupling 40 requires that the coupling seal 42 have a diameter greater than the tube assembly and that the receptacle have sufficient dimensions to accommodate the deformation shape of the coupling seal 42 while under compression. Moreover, the coupling seal 42 is a separate component that must be attached to the end of the tube assembly before creating the seal. Care is required to avoid separating the coupling seal 42 from the tube assembly and to prevent loss of the coupling assembly during handling due to its small size.

In brief overview, the invention relates to a fitting for a fluidic coupling. The fitting includes a tube assembly that includes an inner tube, an intermediate tube formed of a polymeric material and an outer metal tube. The intermediate tube is made from a polymeric material and includes an extruded portion formed during a crimping process. The extruded portion extends away from the end of the tube assembly. During installation of the fitting, the extruded portion of the polymeric tube is deformed against a sealing surface of a coupling body or other device, resulting in a liquid tight face seal between fluid channels defined by the inner tube and the coupling body.

Advantageously, the fitting does not require a ferrule or a separate seal component to establish the fluidic seal. Moreover, the receptacle of the coupling body is not required to have a conical or other specialized port configuration as long as the tube assembly can pass into the coupling body such that the extruded portion of the intermediate tube is compressed against a suitable sealing surface. As the seal is integral with the tube assembly, problems associated with handling small sealing components are avoided. Moreover, the face seal achieved with the fitting substantially reduces or eliminates unswept volume at the fluidic coupling.

Figure 4A:
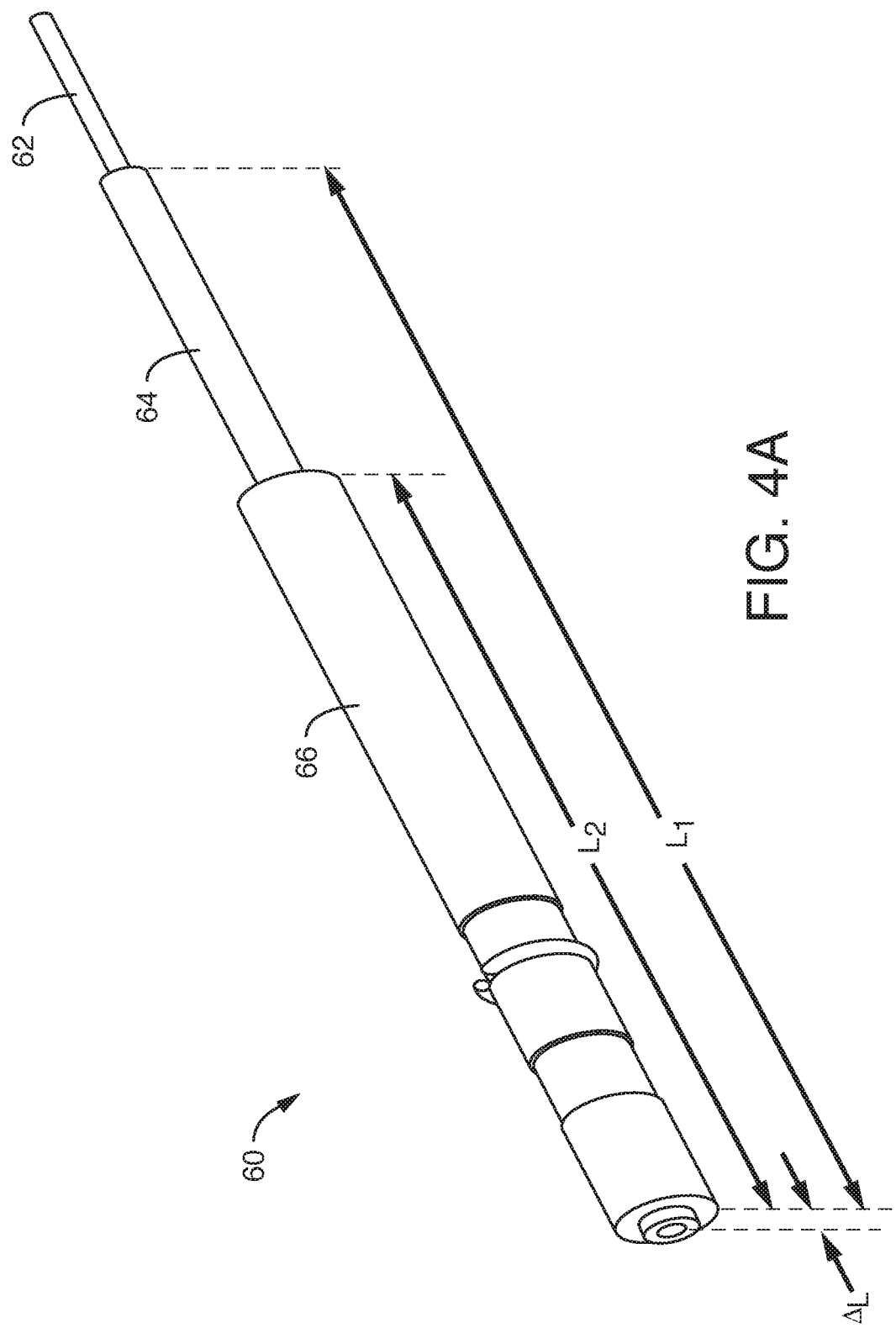
FIG. 4A is a perspective view of a portion of an embodiment of a fitting for a fluidic coupling.
Figure 4B:
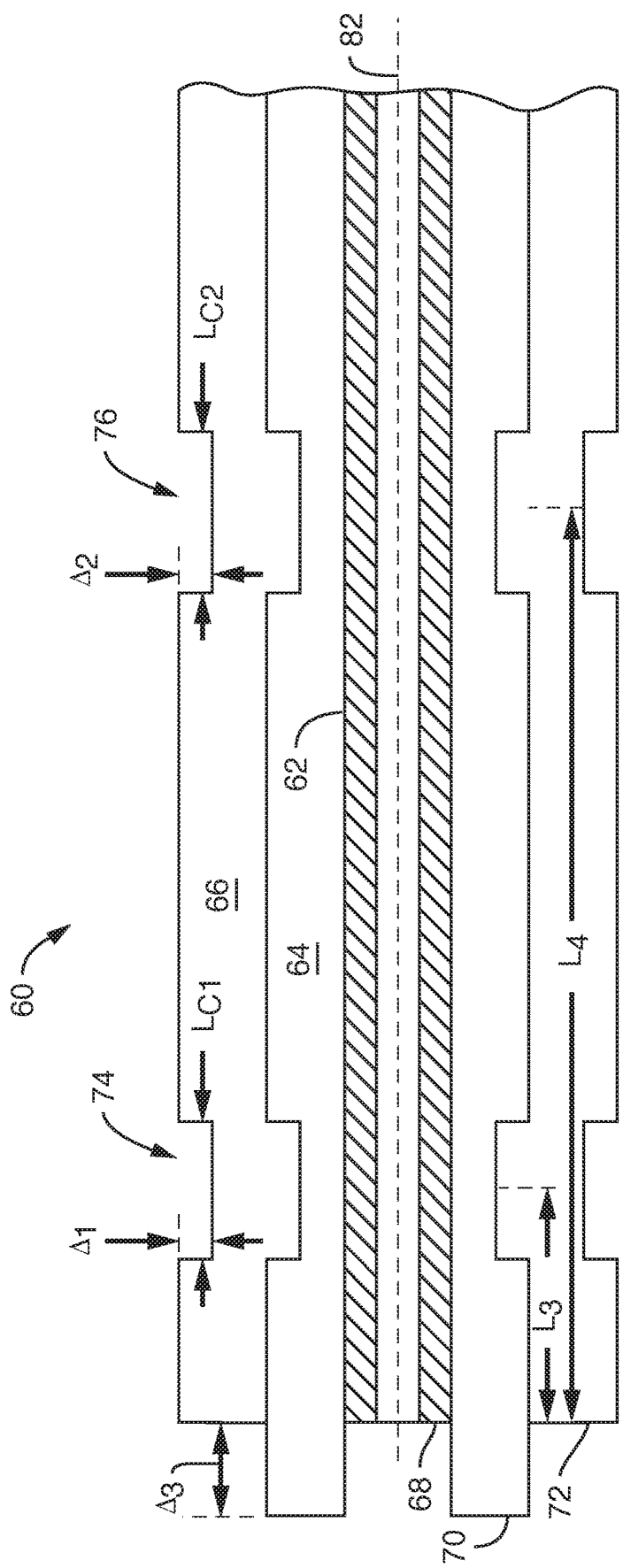
FIG. 4B is a side cross-sectional view of the fitting of FIG. 4A.
Figure 4C:
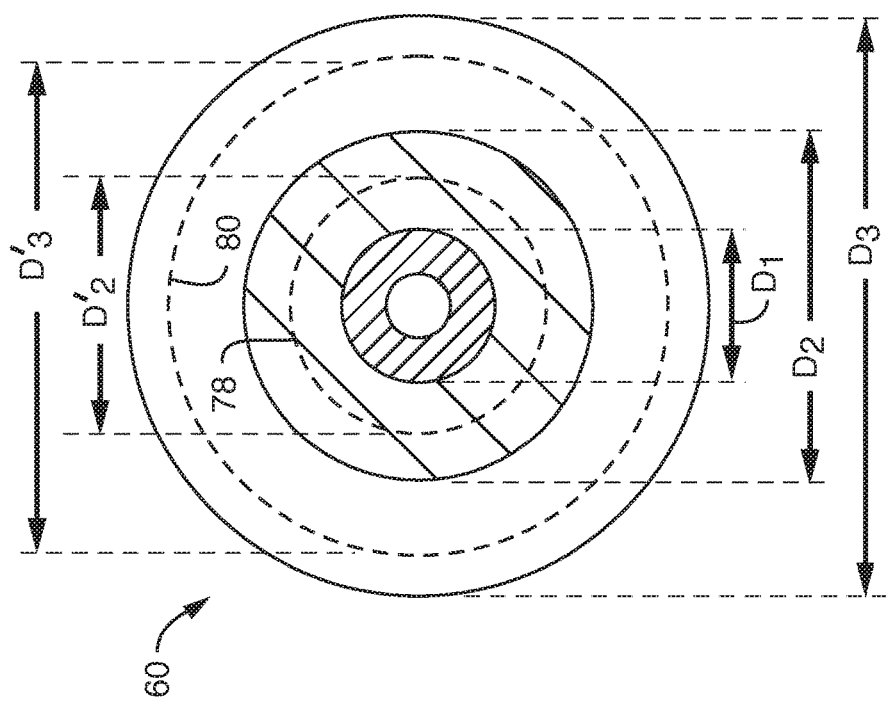
FIG. 4C is an endface view of the fitting of FIG. 4A.

FIGS. 4A, 4B and 4C show a perspective view, a side cross-section view and an endface view, respectively, of a portion of an embodiment of a fitting 60 for a fluidic coupling. The fitting 60 includes a tube assembly having an inner tube 62, an intermediate tube 64 and an outer tube 66. The inner tube 62 includes a fluid channel to be coupled to another fluid channel. Not shown is a compression screw that is used to establish a face seal between an end of the fluid channel an end of another fluid channel. In preferred embodiments, the inner tube 62 is a capillary made of fused silica. In other embodiments, the inner tube 62 may be a different type of glass tube or a metal tube such as a titanium tube or a stainless steel tube. The intermediate tube 64 is formed of a polymeric material such as a thermoplastic polymer (e.g., a polyether ether ketone (PEEK)). The outer tube 66 is preferably a stainless steel tube although metals which are more rigid that the polymeric material and which have suitable material properties (e.g., ductility) may be used. The intermediate tube 64 has an inner diameter that is slightly larger than the outer diameter $D_1$ of the inner tube 62 to permit the intermediate tube 64 to slide over an end of the inner tube 62. The outer tube 66 has an inner diameter slightly larger than the outer diameter $D_2$ of the intermediate tube 64 to allow the intermediate tube 64 (and inner tube 62) to be inserted into the outer tube 66. A positive clearance is provided between the inner tube 62 and the intermediate tube 64, and between the intermediate tube 64 and the outer tube 66. For example, the clearance may be less than 2.5 µm (0.0001 in.) or may be 75 µm (0.003 in) or more. The intermediate tube 64 has a length $L_1$ and the outer tube 66 has a length $L_2$. As illustrated, the length $L_1$ of the intermediate tube 64 exceeds the length $L_2$ of the outer tube 66; however, in other embodiments the lengths $L_1$ and $L_2$ are the same or the length $L_2$ of the outer tube 66 may exceed the length $L_1$ of the intermediate tube 64.

Prior to applying a radial crimping process that yields the illustrated tube assembly, the three tubes 60, 62 and 64 are arranged with respect to each other so that their endfaces 68, 70 and 72, respectively, are co-planar. Preferably, the endfaces 68, 70 and 72 are perpendicular to the tube axes 82 and polished with the endfaces 68, 70 and 72 free of scratches and other surface defects. The fitting 60 is then created by forming on the outer surface of the outer tube 66 a first radial crimp 74 of crimp depth $\Delta_1$ and crimp length $L_{C1}$, and subsequently forming a second radial crimp 76 having a crimp depth $\Delta_2$ and a crimp length $L_{C2}$. As illustrated, the crimp depths $\Delta_1$ and $\Delta_2$ are equal and the crimp lengths $L_{C1}$ and $L_{C2}$ are equal although this is not a requirement. Although shown in FIG. 4B as a near step-like change in diameter of the outer surface of the outer tube 66, in other embodiments the cross-sectional shape of the crimps 74 and 76 may include a more gradual slope for the diameter transition at the left and right crimp edges. In addition, the "bottom" of the crimps 74 and 76 may not be as flat as shown in the figure.

Dashed circles 78 and 80 in FIG. 4C indicate the post-crimp reduced diameters $D_2'$ and $D_3'$, respectively, of the intermediate tube 64 and outer tube 66 in the region of the first radial crimp 74, i.e., at a length $L_3$ from the outer tube endface 72. The first radial crimp 74 acts to secure, or "capture," the inner tube 62 with respect to the intermediate and outer tubes 64 and 66. In addition, the first radial crimp 74 creates a desired strain of the intermediate tube 64 such that the polymeric material flows parallel to the tube assembly axis 82 between the more rigid inner and outer tubes 62 and 66. As a result of the extrusion of the polymeric material, the intermediate tube endface 70 is separated from the inner and outer tube endfaces 68 and 72 by an extrusion length $\Delta_3$. A predetermined extrusion length $\Delta_3$ for the polymeric material is achieved by controlling certain parameters, including the crimp depth $\Delta_1$ and crimp length $L_{C1}$ of the first radial crimp 74 and the distance $L_3$ of the first radial crimp 74 from the inner and outer tube endfaces 68 and 72. In some embodiments, the extrusion length is less than 0.50 mm (0.02 in.).

Figure 5:
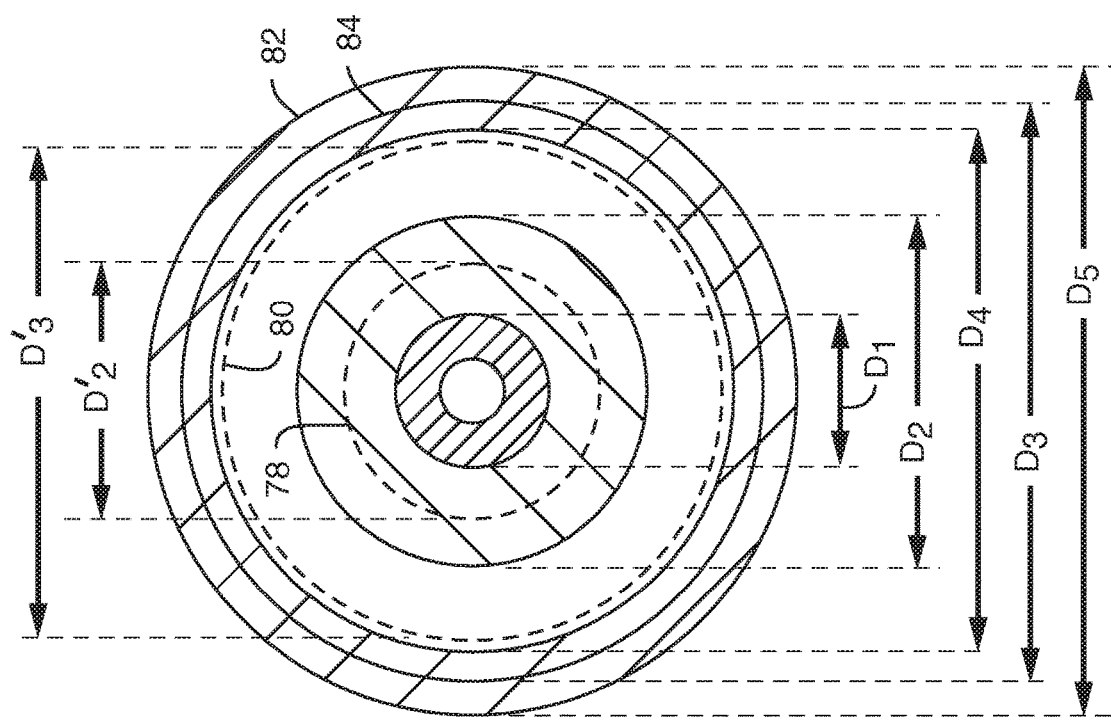
FIG. 5 is a cross-sectional view of the fitting of FIG. 4A along a tube assembly axis at a radial crimp with a retaining ring installed.

After forming the first radial crimp 74, the second radial crimp 76 is formed at a distance $L_4$ from the outer tube endface 72. The second radial crimp 76 enables a retaining ring 83 (e.g., a C-clip) to be installed. FIG. 5 shows a cross-sectional view through the installed retaining ring 83. Circle 84 indicates the outer surface of the outer tube 66 at the outer tube diameter $D_3$. The retaining ring 83 has an inner diameter $D_4$ that is equal to or greater than the crimp diameter $D_3'$ on the outer tube 66 at the second radial crimp 76 and an outer diameter $D_5$ that is greater than the outer tube diameter $D_3$. Thus the retaining ring 83 can be installed at the second crimp 76 and is free to move axially along the length $L_{C2}$ of the crimp 76.

Figure 6A:
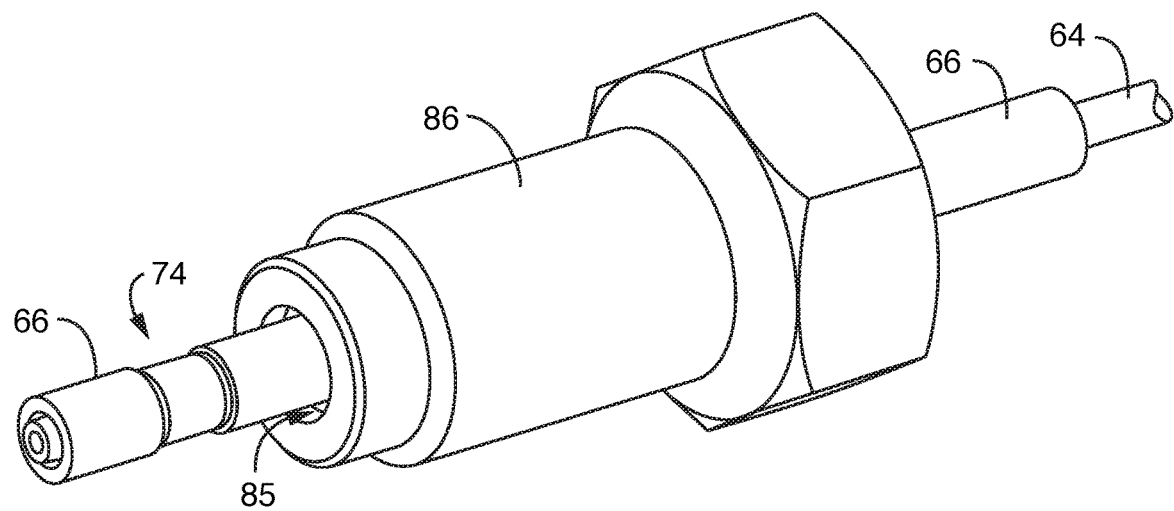
FIG. 6A is a perspective view of a portion of the fitting of FIG. 4A with a compression screw installed.
Figure 6B:
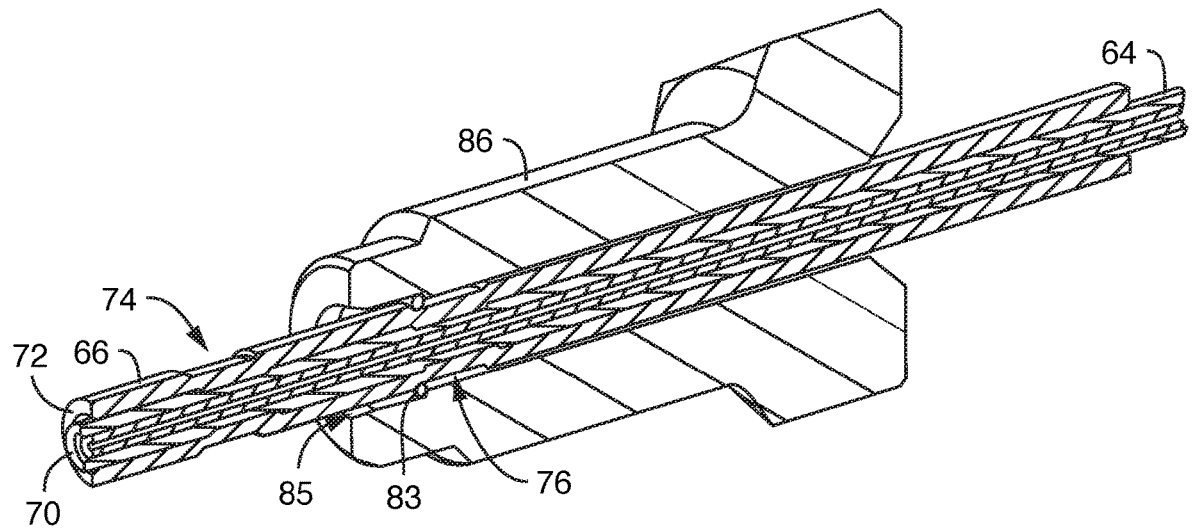
FIG. 6B is a cutaway perspective view of the fitting of FIG. 6A.

Reference is made to FIG. 6A which is a perspective view of a portion of the fitting 60 of FIG. 4A with a compression screw 86 installed and to FIG. 6B which is a cutaway perspective view of the fitting of FIG. 6A. The compression screw 86 has a counterbore that includes a cylindrical hole 85 terminating at a bottom surface. The hole 85 has a diameter that is greater than the outer diameter $D_5$ of the retaining ring 83 when the retaining ring 83 is positioned in the second radial crimp 76 in a relaxed state. The counterbore also includes a through-hole that extends from the bottom surface of the hole 85 to the opposite end of the compression screw 86. The through-hole has a diameter that is greater than the outer tube diameter $D_3$ and less than the outer diameter of the retaining ring 83 in its relaxed state. Thus the compression screw 86 can be inserted over the tube assembly so that the tube assembly passes through the through-hole; however, once the retaining ring 83 is installed at the second crimp 76, the compression screw 86 can be moved axially from right to left in the figure until the bottom surface at the hole 85 engages the retaining ring 83. Further axial movement of the compression screw 86 along the tube assembly is prevented once the compression screw 86 pushes the retaining ring 83 up against the left side of the second crimp 76.

Figure 7:
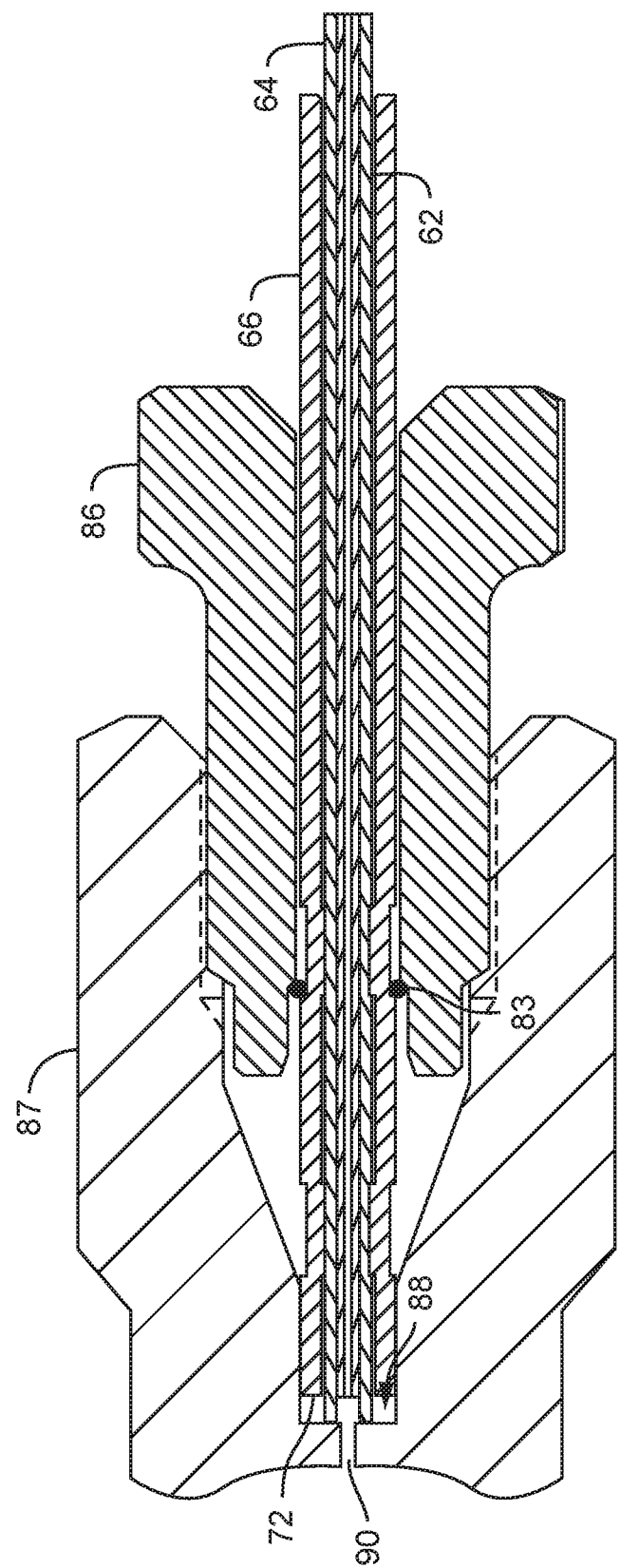
FIG. 7 is a cross-sectional side view showing the fitting of FIG. 4A inserted into a coupling body to achieve a face seal between two fluid channels.

The engagement of the compression screw 86 with the retaining ring 83 is relied upon during the installation of the fitting into a coupling body 87 to achieve a face seal as shown in FIG. 7. The illustrated coupling body 87 includes a counterbore having a hole with a bottom surface 88 and a through-hole extending from the bottom surface 88 that defines a fluid channel 90 to conduct the fluid received from the tube assembly. The hole has a diameter greater than the outer tube diameter $D_3$ to enable the tube assembly to be inserted into the coupling body 87. To seal the two fluid channels, the compression screw 86 engages a threaded bore of the coupling body 87 and is rotated until the bottom surface at the hole 85 in the compression screw 86 comes into contact with the retaining ring 83 as described above. Further rotation of the compression screw 86 moves the retaining ring 83 to the left until the retaining ring 83 comes into contact with the left edge of the second radial crimp 76. Subsequent rotation seats the retaining ring 83 fully into the counterbore of the compression screw 86 then drives the fitting forward to form a face seal as the intermediate tube endface 70 (see FIG. 6B) comes into contact with the bottom surface of the coupling body 87. At this time there is increased resistance to rotation of the compression screw 86. A small additional rotation of the compression screw 86 results in compression of the extruded portion of the polymeric material to provide a fluidic face seal at the intermediate tube endface 70 and the bottom surface 88 inside the coupling body 87.

While the invention has been shown and described with reference to specific preferred embodiments, it should be understood by those skilled in the art that various changes in form and detail may be made therein without departing from the scope of the invention as defined by the following claims. For example, some embodiments described above include a compression screw to advance a tube assembly into a coupling body to achieve an axial compression of the intermediate tube. It will be recognized that other means of achieving compression of the intermediate tube against a sealing surface may be used. In addition, the seating and positioning of the retaining ring can be established prior to threading the compression screw into the coupling body.

What is claimed is:

1. A fitting for a fluidic coupling, comprising:
   a tube assembly comprising:
      an inner tube having an inner tube endface and a first fluid channel;
      an intermediate tube formed of a polymeric material and disposed over at least a portion of a length of the inner tube, the intermediate tube including an extruded portion having a length and an intermediate tube endface; and
      an outer tube formed of a metal and disposed over the intermediate tube, the outer tube having an outer tube endface and an outer surface, a first radial crimp on the outer surface at a first distance from the outer tube endface and extending for a first axial length, and a second radial crimp on the outer surface at a second distance from the outer tube endface and extending for a second axial length, the outer tube endface being co-planar with the inner tube endface, the intermediate tube endface being separated from the inner tube endface and the outer tube endface by the length of the extruded portion.

2. The fitting of claim 1 further comprising a retaining ring disposed on the outer tube at the first radial crimp.

3. The fitting of claim 2 further comprising a compression screw having a first counterbore having a first hole having a first bottom surface and a first diameter that is greater than a diameter of the retaining ring in a relaxed state, the first counterbore having a first through-hole having a second diameter that is less than the diameter of the retaining ring and extending from the first bottom surface, the first bottom surface configured to contact the retaining ring when the compression screw is axially advanced over the tube assembly.

4. The fitting of claim 3 further comprising a coupling body having a second counterbore having a second hole having a second bottom surface and a third diameter that is greater than a diameter of the outer tube, the second counterbore having a second through-hole extending from the second bottom surface and defining a second fluid channel, wherein the intermediate tube endface is in contact with the second bottom surface and the intermediate tube is under compression to thereby seal the first fluid channel to the second fluid channel.

5. The fitting of claim 1 wherein the inner tube endface includes a polished surface.

6. The fitting of claim 1 wherein the inner tube is formed of a glass.

7. The fitting of claim 6 wherein the inner tube is a fused silica capillary.

8. The fitting of claim 1 wherein the inner tube is formed of a metal.

9. The fitting of claim 8 wherein the inner tube is a stainless steel tube.

10. The fitting of claim 1 wherein the intermediate tube is formed of polyether ether ketone.

11. The fitting of claim 1 wherein the outer tube is formed of stainless steel.

12. The fitting of claim 1 wherein the length of the extruded portion of the intermediate tube is less than 0.50 mm.

13. A method of forming a fitting for a fluidic coupling, the method comprising:
    for a tube assembly comprising an inner tube having an inner tube endface and a fluid channel, an intermediate tube formed of a polymeric material and disposed over at least a portion of a length of the inner tube and having an intermediate tube endface, and an outer tube formed of a metal and disposed over the intermediate tube, the outer tube having an outer tube endface and an outer surface, the inner tube endface, intermediate tube endface and outer tube endface being coplanar with each other:
       forming a first radial crimp on the tube assembly over a first crimp length at a first distance from the outer tube endface to secure the inner tube, intermediate tube and outer tube to each other and to extrude a portion of the intermediate tube such that the intermediate tube endface is separated from the inner tube endface and the outer tube endface by an extrusion length; and
       forming a second radial crimp on the tube assembly over a second crimp length at a second distance from the outer tube endface.

14. The method of claim 13 wherein the first radial crimp has a radial depth and wherein the extrusion length is determined in part by the radial depth.

15. The method of claim 13 wherein the extrusion length is determined in part by the first crimp length.

16. The method of claim 13 wherein the extrusion length is determined in part by the first distance from the outer tube endface.

17. The method of claim 13 further comprising polishing at least one of the inner tube endface, the intermediate tube endface and the outer tube endface prior to the forming of the first radial crimp.

* * * * *